United States Patent [19]

Idota et al.

[11] Patent Number: 4,683,189

[45] Date of Patent: Jul. 28, 1987

[54] TONERS FOR SILVER HALIDE DIFFUSION TRANSFER IMAGE WITH SULFO OR CARBOXYL GROUPS

[75] Inventors: Yoshio Idota; Morio Yagihara, both of Kanagawa, Japan

[73] Assignee: Fuji Photo Film Co., Ltd., Kanagawa, Japan

[21] Appl. No.: 853,835

[22] Filed: Apr. 21, 1986

[30] Foreign Application Priority Data

Apr. 19, 1985 [JP] Japan .................................. 60-83664
Apr. 19, 1985 [JP] Japan .................................. 60-83665
Apr. 19, 1985 [JP] Japan .................................. 60-83666

[51] Int. Cl.$^4$ .......................... G03C 5/54; G03C 5/46
[52] U.S. Cl. ..................... 430/248; 430/233, 430/965
[58] Field of Search ............... 430/233, 248, 251, 611, 430/204, 965

[56] References Cited

U.S. PATENT DOCUMENTS

| | | | |
|---|---|---|---|
| 2,698,900 | 10/1972 | Johnson | 430/233 |
| 3,305,362 | 2/1967 | Riester et al. | 430/611 |
| 3,756,825 | 9/1973 | Rickter | 430/233 |
| 4,328,302 | 5/1982 | Nishimura et al. | 430/611 |
| 4,436,805 | 3/1984 | Igochi et al. | 430/233 |
| 4,607,004 | 8/1986 | Ikenoue et al. | 430/611 |

*Primary Examiner*—Richard L. Schilling
*Attorney, Agent, or Firm*—Sughrue, Mion, Zinn, Macpeak & Seas

[57] ABSTRACT

A method of forming a silver salt diffusion transfer image comprises developing an imagewise exposed photosensitive silver halide emulsion layer with a developing agent and a silver halide solvent in the presence of an alkali to thereby convert at least a portion of unexpected silver halide in said emulsion layer to a diffusible silver complex salt and transferring at least a portion of said silver complex salt into a silver precipitating agent-containing image receivin- layer to form an image in said image receiving layer. In the above method said image is formed in the presence of a compound selected from the group consisting of compounds of the general formulae (I), (II) and (III):

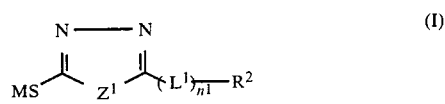

(I)

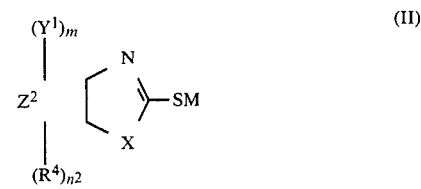

(II)

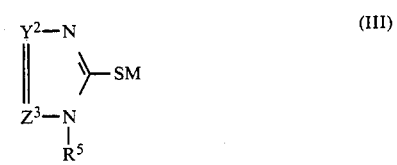

(III)

10 Claims, No Drawings

TONERS FOR SILVER HALIDE DIFFUSION TRANSFER IMAGE WITH SULFO OR CARBOXYL GROUPS

FIELD OF THE INVENTION

This invention relates to a method of forming a silver halide diffusion transfer image and to an integral film unit for use in practicing the method.

BACKGROUND OF THE INVENTION

The technique of forming an image by the diffusion transfer principle employing a silver salt such as a silver halide is well known. The technique comprises treating an imagewise exposed photosensitive silver halide emulsion layer with an alkaline aqueous solution containing a developing agent and a silver halide solvent. The exposed silver halide grains are reduced to silver by the developing agent and the unexposed silver halide grains are converted by the silver halide solvent to a diffusible or transferable silver complex salt. This silver complex salt is diffused and transferred by inhibition to a silver precipitating agent-containing layer (image receiving layer) which is superposed with the emulsion layer to thereby cause the silver complex salt to be reduced by the developing agent in situ with the aid of the silver precipitating agent.

This technique is generally practiced using a film unit which consists of a photosensitive element comprising a support with a photosensitive silver halide emulsion layer disposed thereon, an image receiving element comprising a support with a silver precipitating agent-containing image receiving layer disposed thereon, and a processing element comprising a rupturable container containing an active alkaline aqueous solution containing a developing agent, a silver halide solvent and a rheology modifier. In practice, the silver halide emulsion layer of the photosensitive element is first imagewise exposed and, then, the photosensitive element and image receiving element are superposed in such a manner that their emulsion layer and image receiving layer will be brought together and passed over a pair of rollers in a manner that the processing element is ruptured to release the viscous aqueous solution in the nip zone of the roller pair. The film unit is then allowed to stand for a predetermined time, after which the image receiving element is separated from the photosensitive element so as to provide a print carrying the desired image in the image receiving layer. In such a diffusion transfer process using a silver salt such as silver halide, the silver image obtained is generally not black, but rather assumes a brown or other unacceptable color. It is common practice to use a toning agent so as to overcome this disadvantage of the diffusion transfer process.

An example of a well known toning agent is 1-phenyl-5-mercapto-1,2,3,4-tetrazole. S-substituted pyrimidine derivatives such as those described in U.S. Pat. No. 3,756,825 are known and have been reported to help obtain dark blue images with high optical densities.

The color of the silver image has an important bearing on the quality of the print. The colors of prints available today on the market are not necessarily satisfactory and improvement in this respect has been desired. To this day a toner has not been available that will yield an image of lacquer black shade with a minimum of metallic gloss and high maximum density.

In view of the above circumstances, intensive research has been conducted to develop a method for improving the color of the silver image with the use of a new toner and found that the use of a nitrogen-containing heterocyclic mercaptan compound having a sulfo- or carboxyl-substituted alkyl group or a sulfo- or carboxyl-substituted aryl group enables one to overcome the above-mentioned disadvantages of the prior art.

SUMMARY OF THE INVENTION

An object of this invention is to provide a new method of forming an image by the silver halide diffusion transfer principle.

It is another object of this invention to provide a method of producing an image of desirable lacquer black color.

This invention is directed to a method of forming a silver salt diffusion transfer image comprising developing an imagewise exposed photosensitive silver halide emulsion layer with a developing agent in the presence of a silver halide solvent and an alkaline agent to thereby convert at least a portion of unexposed silver halide in the emulsion layer to a diffusible silver complex salt and causing at least a portion of the silver complex salt to diffuse into a silver precipitating agent-containing image receiving layer to thereby form an image in the image receiving layer, wherein the image is formed in the presence of a compound selected from the group consisting of compounds of the following general formulae (I), (II) and (III).

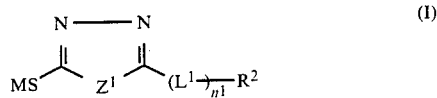

wherein:
$Z^1$ is a sulfur atom, an oxygen atom or

$R^3$ is a hydrogen atom, a substituted or unsubstituted alkyl group with the proviso that the substituent is other than a sulfo or carboxyl group, or a substituted or unsubstituted aryl group with the proviso that the substituent is other than a sulfo or carboxyl group;

$R^2$ is an organic group containing at least one sulfo or carboxyl group;

$L^1$ is —CONR—, —NRCO—, —SO$_2$NR—, —NRSO$_2$—, —OCO—, —COO—, —S—, —NR—, —CO—, —SO—, —SO$_2$—, —OCOO—, —NRCONR$^1$—, —NRCOO—, —OCONR— or —NRSO$_2$NR$^1$—, wherein R and $R^1$ each is hydrogen, alkyl or aryl;

$n^1$ is 0 or 1;

M is a hydrogen atom, an alkali metal atom, a quaternary ammonium group or a quaternary phosphonium group.

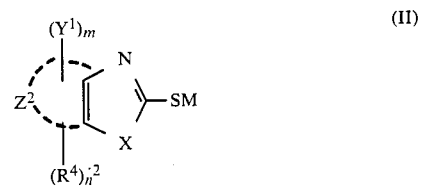

wherein:
X is

or a selenium, sulfur or oxygen atom;
R$^7$ is a hydrogen atom or an alkyl group;
R$^4$ is a substituent group;
Z$^2$ is a group of atoms necessary to complete a carbocyclic or heterocyclic ring;
Y$^1$ is a carboxyl or sulfo group;
M is a hydrogen atom, an alkali metal atom, a quaternary ammonium group or a quaternary phosphonium group;
m is a whole number of 1 to 3;
n$^2$ is a whole number of 0 to 2.

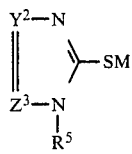
(III)

wherein:
Y$^2$ and Z$^3$, which are the same or different, each is N or CR$^6$ (wherein R$^6$ is a hydrogen atom, a substituted or unsubstituted alkyl group, or a substituted or unsubstituted aryl group);
R$^5$ is an alkyl group substituted by at least one SO$_3$M$^1$ or COOM$^1$ group or an aryl group substituted by at least one SO$_3$M$^1$ or COOM$^1$ group;
M and M$^1$, which are the same or different, each is a hydrogen atom, an alkali metal atom, a quaternary ammonium group or a quaternary phosphonium group.

DETAILED DESCRIPTION OF THE INVENTION

Referring to general formula (I), R and R$^1$ for L$^1$ are respectively a hydrogen atom, an alkyl group (preferably a lower alkyl group such as methyl, ethyl, etc.) or an aryl group (preferably a phenyl group), and the alkyl and aryl groups may be substituted.

The organic group R$^2$ may, for example, be an alkyl group of 1 to 20 carbon atoms (for example, methyl, ethyl, octyl, etc.), an aryl group of 6 to 20 carbon atoms (for example, phenyl, naphthyl, etc.) or an alkyl or aryl group as attached through a linking group such as —S—, —O—,

—CO—, —SO—, —SO$_2$— or the like. R$^2$ includes groups having, in addition to at least one sulfo or carboxyl group, other substituent groups. Among the other substituent groups are alkyl groups (for example, methyl, ethyl, etc.) aryl groups (for example, phenyl), halogen atoms (for example, F, Cl, Br, etc.), alkoxy groups (for example, methoxy, methoxyethoxy, etc.), carbamido groups (for example, acetamido, etc.), sulfonamido groups (for example, methanesulfonamido, etc.), hydroxy groups, sulfamoyl groups (for example, unsubstituted sulfamoyl, methylsulfamoyl, etc.) and so on.

R$^3$ is preferably a hydrogen atom, a substituted or unsubstituted alkyl group of 1 to 20 carbon atoms, or a substituted or unsubstituted aryl group of 6 to 20 carbon atoms, and the substituents may be the same groups as mentioned as substituents for R$^2$.

The following compounds are preferred compounds of the formula (I).

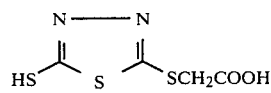
I-1

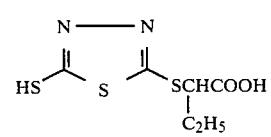
I-2

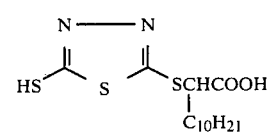
I-3

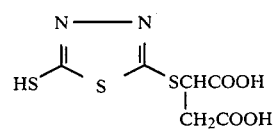
I-4

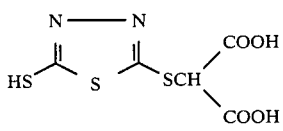
I-5

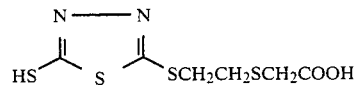
I-6

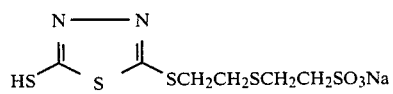
I-7

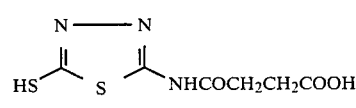
I-8

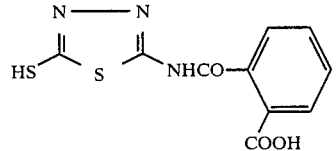
I-9

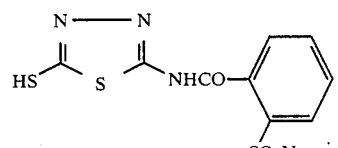
I-10

-continued

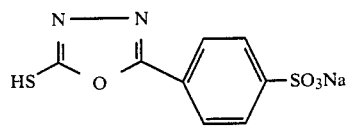  I-11

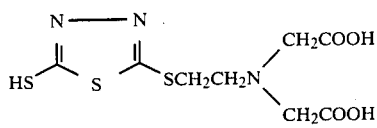  I-12

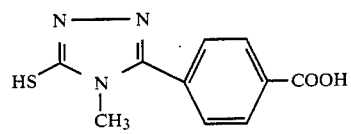  I-13

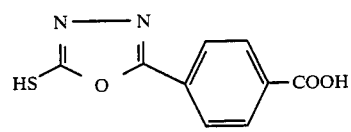  I-14

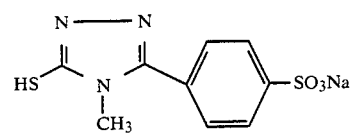  I-15

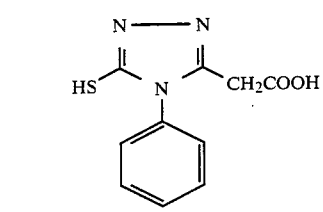  I-16

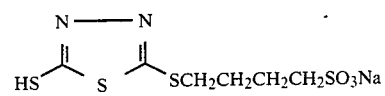  I-17

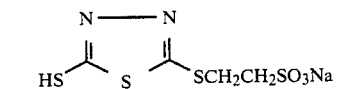  I-18

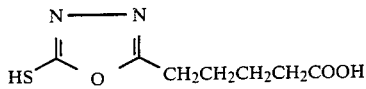  I-19

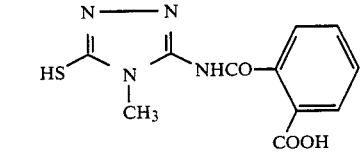  I-20

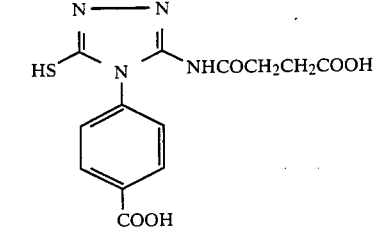  I-21

-continued

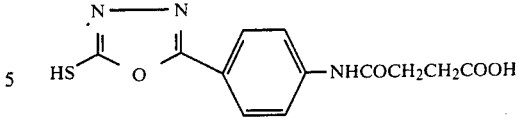  I-22

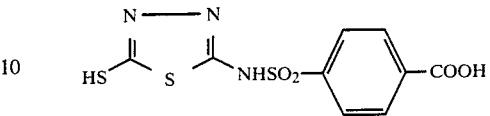  I-23

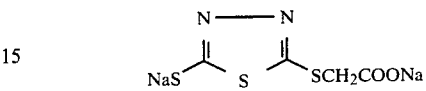  I-24

The above compounds of general formula (I) can be synthesized by known processes described in the following literature: *Journal of American Chemical Society*, 44, 1502–1510, U.S. Pat. Nos. 3,017,270, 3,212,892 (British Patent No. 940,169), Japanese Patent Publication No. 8334/74, U.S. Pat. No. 4,264,721 (Japanese Patent Application (OPI) No. 59463/80 (the term "OPI" as used herein refers to a "published unexamined Japanese patent application")), *Advances in Heterocyclic Chemistry*, 9, 165–209 (1968), *Khim. Geterotikl. Soedin*, 7 (7), 1905–9, and U.S. Pat. No. 4,278,793 (West German Patent No. 2,716,707).

Referring to general formula (II), the carbocyclic or heterocyclic ring formed by $Z^2$ may, for example, be a 5-membered, 6-membered or 7-membered carbocyclic ring or a 5-membered, 6-membered or 7-membered heterocyclic ring containing one or more atoms selected from the group consisting of nitrogen, oxygen, sulfur and other hetero atoms including condensed ring structures formed by such carbocyclic or heterocyclic rings in appropriate planes. Specific examples are benzene, naphthalene, pyridine, pyrimidine, quinoline, isoquinoline and other rings.

$R^7$, which represents a hydrogen atom or an alkyl group, is preferably a hydrogen atom.

The substituent $R^4$ may, for example, be a halogen atom (F, Cl, Br, etc.), a substituted or unsubstituted alkyl group (methyl, ethyl, etc.), a substituted or unsubstituted aryl group (phenyl, p-chlorophenyl, etc.), a substituted or unsubstituted alkoxy group, an aryloxy group (methoxy, methoxyethoxy, phenoxy, etc.), a sulfonyl group (methanesulfonyl, p-toluenesulfonyl, etc.), a sulfonamido group (methanesulfonamido, benzenesulfonamido, etc.), a sulfamoyl group (diethylsulfamoyl, unsubstituted sulfamoyl, etc.), a carbamoyl group (unsubstituted carbamoyl, diethylcarbamoyl, etc.), an amido group (acetamido, benzamido, etc.), a ureido group (methylureido, phenylureido, etc.), an aryloxy- or alkoxycarbonylamino group (methoxycarbonylamino, phenoxycarbonylamino, etc.), an aryloxy- or alkoxycarbonyl group (methoxycarbonyl, phenoxycarbonyl, etc.), a cyano group, a hydroxy group, a carboxyl group, a sulfo group, or a nitro group, and preferably a sulfonyl group, a sulfonamido group, a sulfamoyl group, a carbamoyl group, an amido group, a ureido group, a hydroxy group, a carboxyl group or a sulfo group.

In formula (II), m is a whole number of 1 to 3, n is a whole number of 0 to 2, and the sum of m and n is preferably a whole number equal to 1 to 4.

The following compounds are compounds of the general formula (II).
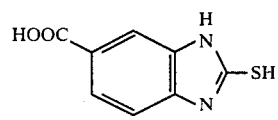 II-1
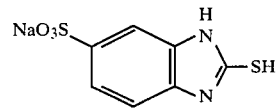 II-2
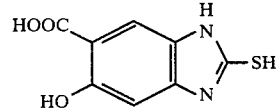 II-3
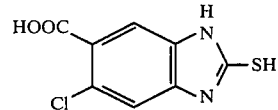 II-4
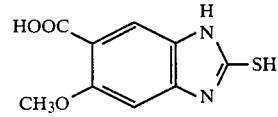 II-5
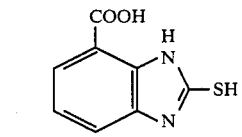 II-6
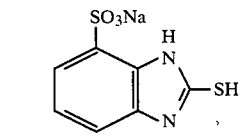 II-7
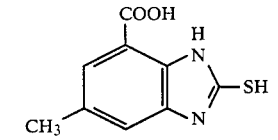 II-8
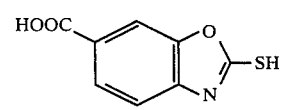 II-9
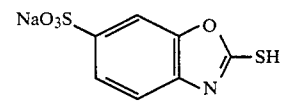 II-10
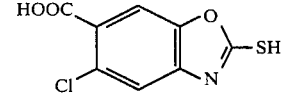 II-11
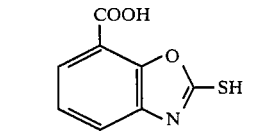 II-12
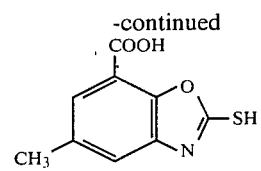 II-13
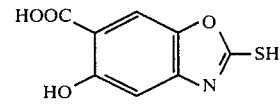 II-14
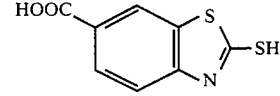 II-15
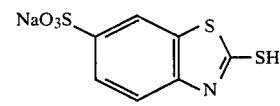 II-16
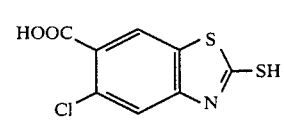 II-17
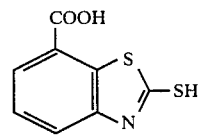 II-18
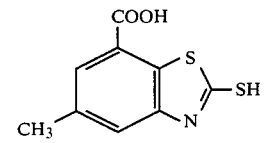 II-19
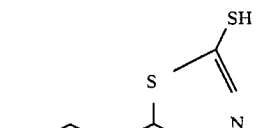 II-20
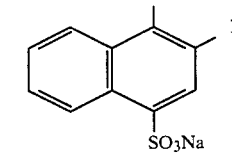 II-21
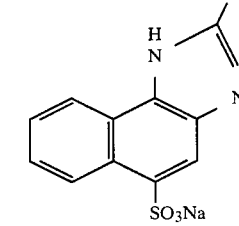 II-22

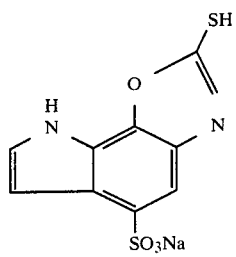

II-23

The compounds represented by general formula (II) can be synthesized by the known processes described in the following literature.

*The Chemistry of Heterocyclic Compounds: Imidazole and Derivatives,* Vol. 1, p. 384, *Organic Syntheses Collective Volume IV,* 569 (1963), *Chemische Berichte,* 9, 465 (1976), *Journal of The American Chemical Society,* 45, 2390 (1923), and Japanese Patent Application (OPI) Nos. 89034/75 and 28426/78 and U.S. Pat. No. 3,666,643 (Japanese Patent Application (OPI) No. 21007/80).

Referring to general formula (III) and, more particularly, to the substituted alkyl group represented by $R^5$, the number of carbon atoms in alkyl-moiety is preferably not more than 20 and, for still better results, is in the range of 1 to 10, and may be substituted by groups other than sulfo and carboxyl groups; for example, halogen atoms, alkoxy groups (preferably those whose alkyl moiety contains 1 to 20 carbon atoms), aryloxy groups (preferably containing 6 to 20 carbon atoms), amido groups, carbamoyl groups, sulfonamido groups, sulfamoyl groups, a cyano group, a hydroxy group, aryl groups (preferably containing 6 to 20 carbon atoms), alkoxycarbonyl groups (preferably containing 2 to 20 carbon atoms), etc.

The substituted aryl group represented by $R^5$, wherein the aryl group is preferably phenyl, may be substituted by groups other than sulfo and carboxyl groups; for example, halogen atoms, alkoxy groups (whose alkyl moiety preferably contains 1 to 20 carbon atoms), aryloxy groups (preferably containing 6 to 20 carbon atoms), amido groups, carbamoyl groups, sulfonamido groups, sulfamoyl groups, a cyano group, a hydroxy group, alkyl groups (preferably containing 1 to 20 carbon atoms), alkoxycarbonyl groups (preferably containing 2 to 20 carbon atoms), etc.

$Y^2$ and $Z^3$ are preferably both N or both $CR^6$. $R^6$ is preferably a substituted or unsubstituted alkyl group of 1 to 20 carbon atoms or a substituted or unsubstituted aryl group of 6 to 20 carbon atoms, more preferably a substituted or unsubstituted alkyl group of 1 to 10 carbon atoms or a substituted or unsubstituted aryl group of 6 to 15 carbon atoms.

The following compounds are compounds represented by general formula (III).

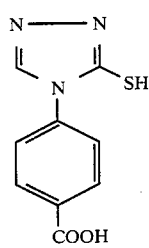

III-1

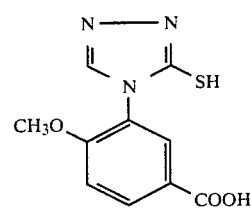

III-2

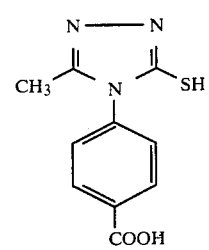

III-3

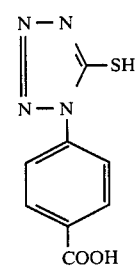

III-4

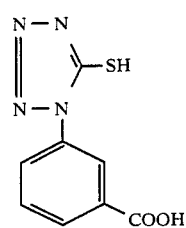

III-5

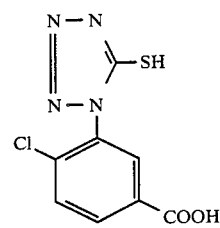

III-6

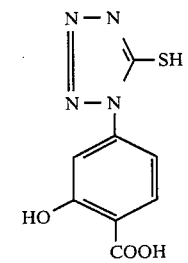

III-7

-continued
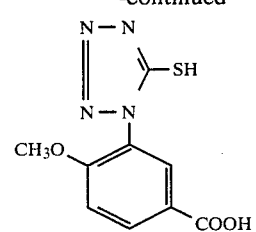
III-8
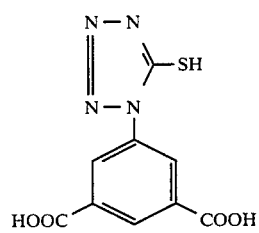
III-9
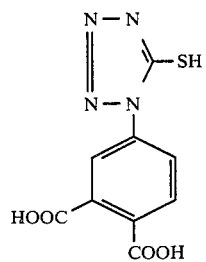
III-10
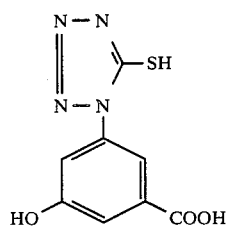
III-11
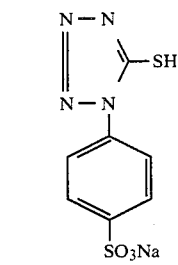
III-12
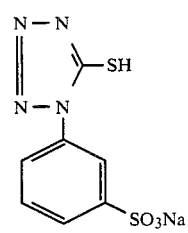
III-13
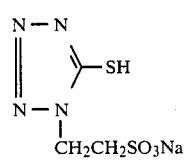
III-14
-continued
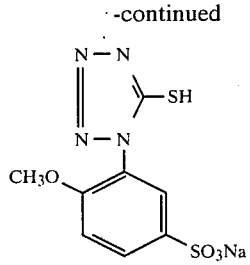
III-15
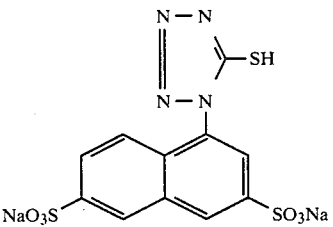
III-16
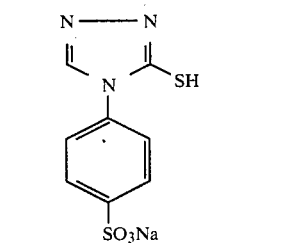
III-17
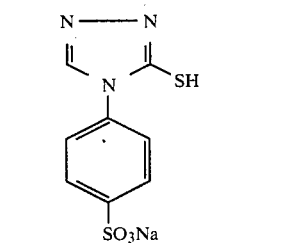
III-18
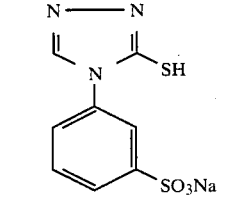
III-19
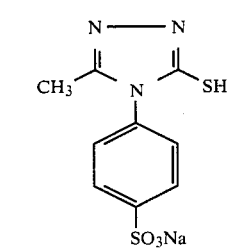
III-20
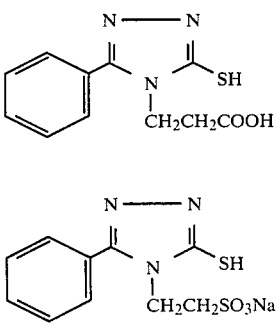
III-21

III-22 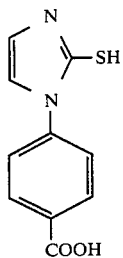

III-23 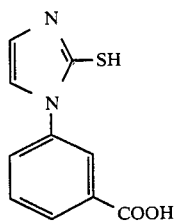

III-24 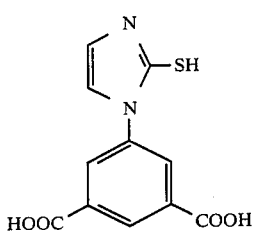

III-25 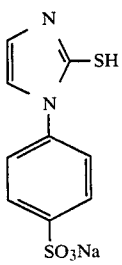

III-26 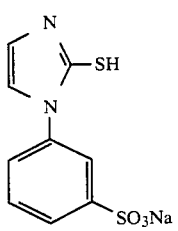

III-27 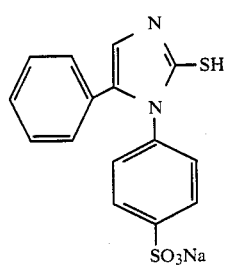

III-28 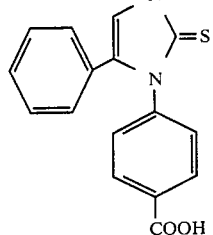

III-29 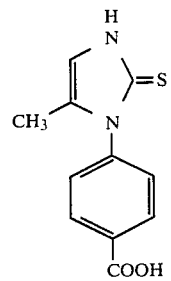

As regards the synthesis of compounds represented by the general formula given above, they can be easily synthesized starting with an isothiocyanate in the well known manner.

The following is a partial list of the literature describing pertinent synthetic processes that may be used.

U.S. Pat. Nos. 2,585,388, 2,541,924 and 3,266,897 (Japanese Patent Publication No. 21842/67), Japanese patent application (OPI) No. 50169/78, British Patent 1,275,701, D. A. Berges et al., *Journal of Heterocyclic Chemistry*, 15, 981 (1978), *The Chemistry of Heterocyclic Compounds, Imidazole and Derivatives*, Part I, pp. 336–339, *Chemical Abstract*, 58, 7921 (1963), p. 394, E. Hoggarth, *Journal of Chemical Society*, 1949, pp. 1160–1167, E. S. Sandler & W. Karo, *Organic Functional Group Preparation*, Academic Press, 1968, pp. 312–315, I. I. Kovtunovskaya Levshine, *Tr. Ukr. Inst. Eksperim Endokrinol.*, 18, 345 (1961), M. Chamdon et al., *Bull. Soc. Chim. Fr.*, 723 (1954), D. A. Shirley & D. W. Alley, *J. Amer. Chem. Soc.*, 79, 4922 (1957), and A. Wohl, W. Marckwald, *Chemische Berichte*, 22, 568 (1889).

The compounds of general formulae (I), (II) and (III) may be present at any stage in the image forming process. Usually, it is incorporated in the photosensitive element having a photosensitive silver halide layer, the image receiving element including a silver precipitating agent-containing image receiving layer, and/or a processing composition, although it is preferably added to the image receiving element or the processing composition and, for best results, to the processing composition.

When the compounds are used in a processing composition, the proportion of the compounds is preferably $10^{-4}$ to 1 g, more preferably in the range of $5 \times 10^{-4}$ to 0.5 g, and most preferably in the range of $10^{-3}$ to 0.2 g, per 100 g of the processing composition.

When the compounds are to be incorporated in the image receiving layer, their proportion is preferably $10^{-4}$ to 1 g/m$^2$, more preferably in the range of $5 \times 10^{-4}$ to 0.5 g/m$^2$, and most preferably in the range of $10^{-3}$ to 0.2 g/m$^2$. In the photosensitive element, they are preferably present in a proportion of $10^{-5}$ to 0.5 g, more preferably in the range of $10^{-4}$ to 0.2 g, and most preferably in the range of $3 \times 10^{-4}$ to 0.1 g per square meter of the face of the element.

In the image forming method and film unit of this invention, the developing agent may be present in the photosensitive element or the processing composition. The developing agent may, for example, be an organic compound in the benzene or naphthalene series which has a hydroxy group and/or an amino group in para- and/or ortho-position, such as hydroquinone, tert-butylhydroquinone, p-aminophenol and so on.

It is also instrumental to employ a reductic acid as described in U.S. Pat. No. 3,615,440 or an $\alpha,\beta$-enediol compound as mentioned in U.S. Pat. No. 3,730,716. Furthermore, hydroxylamine developing agents such as described in U.S. Pat. Nos. 3,287,125 and 3,293,034 can be used with great advantage.

The amount of the developing agent is preferably in the range of 0.1 to 40 g and most desirably in the range of 1 to 20 g to 100 g of the processing composition.

As the developing agent, a 1-aryl-3-pyrazolidinone compound such as mentioned in U.S. Pat. No. 3,740,221 (Japanese Patent Publication No. 13580/74) may be used in combination with the aforementioned developing agents.

The silver halide solvent may be included in the processing composition, photosensitive element and/or image receiving element. It is most desirably present in the processing composition. As such solvent, the cyclic compounds mentioned in U.S. Pat. Nos. 2,857,274, 2,857,275 and 2,857,276 are suitable, and particularly uracil, urazole, 6-methyluracil, etc., are among preferred solvents.

Further, alkali metal thiosulfates, particularly sodium and potassium thiosulfates, are preferable. The silver halide solvent can also be selected from among such compounds as the disulfonylmethane compounds described in U.S. Pat. Nos. 3,958,992, 3,976,647, 4,009,167, 4,032,538, 4,046,568, 4,047,954, 4,047,955 and 4,107,176; the disulfonylmethane compounds mentioned in U.S. Pat. No. 3,769,014 (Japanese Patent Application (OPI) No. 330/72), the thioether-containing dihydroxy pyrimidine compounds described in U.S. Pat. Nos. 4,126,459, 4,150,228, 4,211,559 and 4,211,562; and the amino-thioether compounds mentioned in U.S. Pat. Nos. 4,251,617, 4,267,254 and 4,267,256. These compounds can be used either alone or in combination. The combined use of two or more different cyclic imides or thioether-containing dihydroxy pyrimidine compounds offers the advantage that white precipitates will not separate out on the surface of the print even after prolonged storage.

The amount of the silver halide solvent is preferably in the range of 0.1 to 30 g per 100 g of the processing composition and the most preferred proportion is 0.5 to 10 g per the same basis.

When the processing composition in the practice of this invention is to be used as a thin layer spread between the superimposed photosensitive element and image receiving element, the processing composition preferably contains a polymeric film forming agent, a rheology modifier such as a thickener or a viscosity builder. Hydroxyethyl cellulose and carboxymethyl cellulose sodium are especially useful for this purpose and can be incorporated in the processing composition at an effective concentration conducive to an appropriate rheologic behavior according to the known principle of diffusion transfer photography. In the processing composition, there may be further incorporated other auxiliary agents, such as antifoggants, toning agents, stabilizers, etc., which are known to those skilled in the art of silver halide diffusion transfer photography. The incorporation of a hydroxyethylamino compound such as triethanolamine is particularly beneficial in that it prolongs the pot life of the processing composition as pointed out in U.S. Pat. No. 3,619,185.

The above processing composition is preferably contained in a rupturable container to provide a processing element. The rupturable container as well as its material may be any of the known containers and container materials as described in, for example, U.S. Pat. Nos. 3,056,491, 3,056,492, 3,173,580, 3,750,907, 3,833,381, 4,303,750 and 4,303,751.

The image receiving element of this invention includes a support for supporting a silver precipitating agent-containing image receiving layer, such as one made of baryta paper, cellulose triacetate or polyester. Such an image receiving layer can be prepared by coating the support, which may be primer-coated to give a subbing layer, with a coating dope comprising a dispersion of the silver precipitating agent in an appropriate cellulose ester vehicle such as cellulose diacetate. The cellulose ester layer thus formed is hydrolyzed with alkali to convert at least a part, depthwise or in the thickness direction, of the cellulose ester to cellulose. In an especially useful embodiment, the unhydrolyzed part of the cellulose ester layer containing the silver precipitating agent, such as the cellulose diacetate layer, preferably contains one or more mercapto compounds conducive to improvements in the color, stability and other photographic quality parameters of the transferred silver image. Such mercapto compounds are made available as they migrate from their initial positions in the course of imbibition. Image receiving layers of this type are described in U.S. Pat. No. 3,607,269.

Suitable examples of the silver precipitating agent are heavy metals such as iron, lead, zinc, nickel, cadmium, tin, chromium, copper, cobalt, etc., and, in particular, noble metals such as gold, silver, platinum and palladium. Other useful silver precipitating agents are sulfides and selenides of heavy metals, particularly the sulfides of mercury, copper, aluminum, zinc, cadmium, cobalt, nickel, silver, lead, antimony, bismuth, cerium, magnesium, gold, platinum and palladium and the selenides of lead, zinc, antimony and nickel. The roles which various materials such as silver precipitating agents play in the silver salt diffusion transfer photographic process are described in, for example, U.S. Pat. No. 2,774,667.

An intermediate layer is preferably provided between the image receiving layer and a layer containing the toning agent and stabilizer. Preferred materials of the intermediate layer include gum arabic, polyvinyl alcohol and polyacrylamide.

A release layer is preferably disposed on the surface of the image receiving layer so as to prevent adhesion of the processing composition to the surface of the image receiving layer during separation of the elements after spreading of the processing composition. Preferred materials of the release layer include gum arabic, hydroxyethyl cellulose, methyl cellulose, polyvinyl alcohol, polyacrylamide, and sodium alginate, as well as the materials described in U.S. Pat. Nos. 3,772,024 and 3,820,999 and British Patent 1,360,653.

The compound represented by formula (I), (II) or (III) is preferably incorporated in the coating dope for preparation of the intermediate layer and/or release layer of the image receiving element or in the saponifying composition for alkaline hydrolysis.

In an embodiment of this invention, the image receiving layer may be part of the photosensitive element as described below. For example, a preferred construction consists of a polyethylene terephthalate sheet and, as successively disposed thereon, an image receiving layer containing a silver precipitating agent, a light reflecting layer containing a white pigment such as titanium dioxide, a light-opaque layer containing a light absorbing material such as carbon black, and a photosensitive silver halide emulsion layer. In this embodiment, the image formed in the image receiving layer can be viewed through the polyethylene terephthalate sheet without peeling off the photosensitive silver halide emulsion layer after diffusion transfer processing because the light reflecting layer masks the layers behind from the viewer.

A photosensitive element prepared by coating a photosensitive silver halide emulsion onto a support can also be employed advantageously.

In the photosensitive silver halide emulsion employed according to this invention, any of silver bromide, silver iodobromide, silver iodochlorobromide, silver chlorobromide, and silver chloride can be utilized. Silver iodobromide or silver iodochlorobromide with a silver iodide content not more than 10 mol% is preferred. Silver iodobromide containing 3 to 10 mol% of silver iodide is most preferred.

There is no limitation on the average size of silver halide grains in the photosensitive emulsion (the average diameter when the grains are spherical or near spherical and the average length of edges when the grains are cubic; the average grain size is the average projected area of grains). However, the average grain size is preferably not greater than 3 μm, more preferably not greater than 1.5 μm, and most preferably in the range of 0.8 to 1.2 μm.

The grain size distribution may be broad or narrow.

The silver halide grains in the photosensitive emulsion may be orthogonal crystals such as cubes, octahedral, etc., irregular crystals such as spheres, plates, etc., or composites of them. They may also occur as a mixture of grains having such varied shapes.

The silver halide grain may be heterogeneous as to the surface and interior part thereof or may be homogeneous throughout. It may be a grain such that the latent image is mainly formed on the surface or one in which the latent image is mainly formed in its interior portion. Preferred are grains wherein the latent image is formed on the surface.

The thickness of the photosensitive emulsion layer is 0.5 to 8.0 μm and is preferably 0.6 to 6.0 μm. The coating amount or coverage of silver halide grains in this layer is 0.1 to 3 g/cm² and is preferably 0.2 to 1.5 g/m².

The photosensitive emulsion is prepared by the routine procedure for preparation of silver halide photographic emulsions and subjected to chemical sensitization and spectral sensitization as necessary. In the photosensitive silver halide emulsion may be incorporated such additives as antifoggants, stabilizers, film hardening agents, coating auxiliaries, antistatic agents and so on. The vehicle for the emulsion may, for example, be a gelatin solution.

The compound represented by the formula (I), (II) or (III) to be used in the practice of this invention is preferably included in the coating dope for the silver halide emulsion layer and/or that for the surface protective layer.

Exposure for producing a photographic image may be effected by the conventional method. Thus, any of the various known light sources such as natural light (daylight), tungsten light, fluorescent light, mercury vapor light, xenon arc light, carbon arc light, xenon flash light, cathode ray tube flying spot light and so on can be employed. Exposure time may be 1/1,000 to 1 second, the range which is used with the ordinary camera, or may be shorter, e.g., 1/10⁴ to 1/10⁶ which is obtainable with a xenon flash lamp or a cathode ray tube. It is also possible to use an exposure time in excess of 1 second. If necessary, the spectral distribution of exposure light may be modulated by means of color filters. Laser beams can also be used for exposure purposes. Exposure may also be accomplished by means of light emitted by a fluorescent body as it is excited by electronic rays, X-rays, γ-rays, α-rays, etc.

Regarding the format in which the above described photosensitive element, image receiving element and processing element are arranged to provide an integral film unit, one may refer to the detailed description of such formats in *Neblette's Handbook of Photography and Reprography*, 7th Ed., pp. 282–285. A few particularly desirable formats have also been described in U.S. Pat. No. 3,350,991.

The method for synthesizing the compounds according to this invention is described in detail below.

Unless otherwise indicated all percentages, parts and ratios in the following examples are by weight.

SYNTHESIS EXAMPLE 1

Synthesis of Compound III-4

20 g of 4-carboethoxyphenyl isothiocyanate and 6.5 g of sodium azide are added to water and heated at 80° C. After 2 hours of reaction, the reaction mixture is filtered, cooled and acidified with hydrochloric acid to give crystals of 1-(4-carboethoxyphenyl)-5-mercaptotetrazole. To the crystals are added 5 equivalents of sodium hydroxide (1N NaOH in water) and the mixture is heated at 80° C. for 5 hours. After cooling, the reaction mixture is acidified with hydrochloric acid to cause crude crystals of Compound III-4 to separate out. The crystals are recrystallized from methanol. Yield: 55%, m.p. about 195° C. (decomposed).

SYNTHESIS EXAMPLE 2

Synthesis of Compound III-13

In 300 ml of water is dissolved 23.8 g of sodium azide and the solution is heated at 80° C. A warmed aqueous solution of sodium 3-sulfophenyl isothiocyanate is then added dropwise to the above solution. After completion of dropwise addition, the mixture is reacted for 30 minutes, at the end of which time it is cooled, filtered, and acidified with hydrochloric acid. Then, NaCl is added so as to precipitate the reaction product. The crystals thus obtained are recrystallized from an aqueous solution of NaCl acidified with HCl. The desired Compound III-13 is obtained as monohydrate. Yield: 32%, m.p.: >270° C..

SYNTHESIS EXAMPLE 3

Synthesis of Compound III-22

(1) Synthesis of N-(4-Carboethoxyphenyl)-N'-(2,2-diethoxyethyl)thiourea:

In 50 ml of carbon tetrachloride is dissolved 20 g of 4-carboethoxyphenyl isothiocyanate followed by dropwise addition of 13 g aminoacetaldehyde diethyl acetal over a period of 5 minutes. Then, the mixture is stirred at room temperature for 1 hour. After stirring is completed, 50 ml of carbon tetrachloride is added to the reaction mixture and the resulting crystals are recovered by filtration, washed with 50 ml of carbon tetrachloride, and dried. Yield: 27.5 g, percent yield: 80.9%.

(2) Synthesis of 1-(4-Carboxyphenyl)-2,3-dihydroimidazole-2-thione:

To 80 g of N-(4-carboethoxyphenyl)-N'-(2,2-diethoxyethyl)thiourea synthesized according to step (1) above is added 400 ml of 30% sulfuric acid and the mixture is refluxed on an oil bath for 1 hour. After the reaction mixture is cooled to room temperature, 600 ml of water is added and the mixture is ice-cooled. The resulting crystals are recovered by filtration, washed with 200 ml of water, 100 ml of isopropyl alcohol and 100 ml of hexane in the order mentioned, and dried. Yield: 48 g, percent yield: 92.8%.

In accordance with this invention, an image having a satisfactory color tone (lacquer black) can be obtained in the presence of a compound of the general formulae given hereinbefore, and especially the use of the compound in the processing composition yields advantageous effects, i.e., lack of metallic gloss and an increased maximum density.

The following examples are intended to illustrate this invention in further detail and should by no means be construed as limiting the scope of the invention.

EXAMPLE 1

Photosensitive Sheet

Silver halide grains were prepared by the single jet process and subjected to physical ripening, desalting and chemical ripening to give a silver iodobromide emulsion (iodine content 5.5 mol%). The average diameter of silver halide grains in this emulsion was 0.9 micron, and 1 kg of the emulsion contained 0.65 mol of silver halide. 1 kg aliquots of the emulsion were put into pots and dissolved in a constant temperature bath at 50° C.. To each pot were added the sensitizing dye 3-{5-chloro-2-[2-ethyl-3-(3-ethyl-2-benzothiazolinylidene)-propenyl]-3-benzoxazolio}propane sulfonate, the panchromatic sensitizing dye 4-{2-[3-ethylbenzothiazolin(2-ylidene)-2-methyl-1-propenyl]-3-benzothiazolio}butane sulfonate, 10 ml of an aqueous solution containing 1 wt% of 4-hydroxy-6-methyl-1,3,3a,7-tetraazaindene, 10 ml of an aqueous solution containing 1 wt% of 2-hydroxy-4,6-dichlorotriazine sodium salt, 10 ml of an aqueous solution containing 1 wt% of sodium dedecylbenzenesulfonate, and 10 ml of a methanolic solution containing 0.1 wt% of lipoic acid, and the mixture was stirred at 40° C.. This emulsion was coated on a subbed titanium dioxide-containing polyethylene terephthalate film base to give a 3 micron thick (on a dry basis) layer. Separately, a polymethyl methacrylate latex (average particle size: 3.5 μm) was added to an aqueous solution of gelatin and the mixture was coated over the above layer to give a 1 micron thick (dry) layer. The silver coverage was 0.5 g/m².

Image Receiving Sheet

A polyethylene laminated paper sheet was coated with a solution containing 18 g of cellulose acetate (54% acetylation) and 12 g of styrene-maleic anhydride copolymer or acrylic acid-alkyl acrylate copolymer in a mixture of 270 ml acetone and 30 ml methanol at a coverage of 54 ml/m², followed by drying. Then, a solution of 3,6-diphenyl-1,4-dimercapto-3H,6H-2,3a,5,6a-tetraazapentalene (0.05 g/m²) in a 10% solution of cellulose acetate in acetone was coated on the above layer at a coverage of 10 g (dry)/m². Thereafter, an aqueous solution of dimethylolurea (5%) and acetic acid (50%) were added to a 5% aqueous solution of polyacrylamide at concentrations of 5% and 1.25%, respectively, and the mixture was coated in a thickness of 25 ml/m² on the above layer. Then, a fine dispersion of palladium sulfide in a 3% solution of cellulose acetate in acetone-methanol (9:1) was further coated. In this palladium sulfide dispersion was incorporated 1-phenyl-5-mercaptoimidazole in an amount necessary to give a coverage of $1.25 \times 10^{-6}$ mol/m². The dry thickness of this layer was 0.8 μm. Finally, the following alkali solution was coated on the above layer at the rate of 18 ml/m², followed by aqueous washing and drying to give an image receiving sheet. The above palladium sulfide dispersion was prepared by adding a methanolic solution containing $7 \times 10^{-3}$ mol of sodium sulfide and a methanolic solution containing $7 \times 10^{-3}$ mol of sodium salt of chloro-palladium-complex to a 5.3% solution of cellulose acetate in acetone-methanol (9:1) and stirring the mixture thoroughly.

| Processing Composition | |
| --- | --- |
| Potassium Hydroxide (85%) | 260 g |
| Titanium Dioxide | 3 g |
| Uracil | 45 g |
| 6-Methyluracil | 45 g |
| Hydroxyethyl Cellulose | 70 g |
| Zinc Oxide | 10 g |
| N,N—Bismethoxyethylhydroxylamine | 50 g |
| Triethanolamine | 7 g |
| Tetrahydropyrimidinethione | 0.4 g |
| 2,4-Dimercaptopyrimidine | 0.35 g |
| 6-n-Propylthiouracil | 0.35 g |

To the above composition was added 0.1 g of one of the compounds listed in Table 1, followed by dilution with water to make a total of 2 kg. The resulting processing composition was spread between the above mentioned photosensitive sheet and image receiving sheet, and after an interval of 45 seconds, the sheets were separated.

The color, maximum density and relative sensitivity (D=0.6) are shown in Table 1. The minimum density was invariably 0.10.

TABLE 1

| Example No. | Compound | Color | Maximum Density | Relative Sensitivity | Remarks |
| --- | --- | --- | --- | --- | --- |
| 1-1 | I-1 | Lacquer Black | 1.75 | 99 | Invention |
| 1-2 | I-2 | " | 1.68 | 103 | " |
| 1-3 | I-5 | " | 1.70 | 100 | " |
| 1-4 | I-6 | " | 1.72 | 98 | " |
| 1-5 | I-7 | " | 1.67 | 105 | " |
| 1-6 | I-11 | " | 1.65 | 100 | " |

TABLE 1-continued

| Example No. | Compound | Color | Maximum Density | Relative Sensitivity | Remarks |
|---|---|---|---|---|---|
| 1-7 | I-12 | " | 1.72 | 100 | " |
| 1-8 | I-15 | " | 1.67 | 102 | " |
| 1-9 | I-18 | " | 1.72 | 101 | " |
| 1-10 | I-23 | " | 1.66 | 103 | " |
| 1-11 | No Addition | Bluish Gray | 1.60 | 100 | Control |
| 1-12 | 2,5-Dimercapto-1,3,4-thiadiazole | Gray | 0.78 | — | Comparison |
| 1-13 | 2,5-Dimercapto-1,3,4-oxadiazole | " | 1.05 | 115 | " |

As regards the metallic gloss of the print surface after separation at 5 minutes, only the "no addition" Control Sample 1-11 showed a metallic gloss, with none of the other samples showing a metallic gloss.

It is apparent from Table 1 that with Samples 1-1 to 1-10 containing compounds of this invention there is obtained a lacquer black color as well as a high maximum density which, in particular, is higher than that of the "no addition" Control 1-11.

The symbol "—" in the relative sensitivity column of Tables 1, 2, 3, 7, 8 and 9 indicates that because of an extremely low maximum density value, it is meaningless to make a comparison.

EXAMPLE 2

In the silver iodobromide emulsion layer of the photosensitive sheet described in Example 1 was incorporated one of the compounds listed in Table 2 in a proportion of 0.05 mg/m². The processing composition was prepared in the same manner as in Example 1, except a compound of the present invention was not used. This processing composition was spread between the sheets as in Example 1. The results are shown in Table 2.

TABLE 2

| Sample No. | Compound | Color | Maximum Density | Relative Sensitivity | Remarks |
|---|---|---|---|---|---|
| 2-1 | I-1 | Lacquer Black | 1.65 | 105 | Invention |
| 2-2 | I-5 | " | 1.63 | 107 | " |
| 2-3 | I-7 | " | 1.65 | 104 | " |
| 2-4 | I-12 | " | 1.65 | 103 | " |
| 2-5 | I-18 | " | 1.63 | 105 | " |
| 2-6 | No Addition | Bluish Gray | 1.60 | 100 | Control |
| 2-7 | 2,5-Dimercapto-1,3,4-thiadiazole | Gray | 0.69 | — | Comparison |
| 2-8 | 2,5-Dimercapto-1,3,4-oxadiazole | " | 0.88 | 120 | " |

It is apparent from Table 2 that with Samples 2-1 to 2-5 containing compounds of this invention, there can be obtained not only a lacquer black color but also a high maximum density of print.

EXAMPLE 3

In the intermediate layer of the image receiving sheet of Example 1 was incorporated one of the compounds listed in Table 3 at a level of 3 mg/m². A processing composition was prepared in the same manner as in Example 1, except a compound of the present invention was not used.

The processing composition was spread between the sheets in the same manner as in Example 1. The results are shown in Table 3.

TABLE 3

| Sample No. | Compound | Color | Maximum Density | Relative Sensitivity | Remarks |
|---|---|---|---|---|---|
| 3-1 | I-1 | Lacquer Black | 1.65 | 100 | Invention |
| 3-2 | I-5 | " | 1.65 | 102 | " |
| 3-3 | I-7 | " | 1.64 | 100 | " |
| 3-4 | I-12 | " | 1.65 | 103 | " |
| 3-5 | I-18 | " | 1.63 | 105 | " |
| 3-6 | No Addition | Bluish Gray | 1.60 | 100 | Control |
| 3-7 | 2,5-Dimercapto-1,3,4-thiadiazole | Gray | 0.62 | — | Comparison |
| 3-8 | 2,5-Dimercapto-1,3,4-oxadiazole | " | 0.90 | 132 | " |

It is apparent from Table 3 that with Samples 3-1 to 3-5 containing compounds of this invention a lacquer black color and high maximum density values were obtained, whereas Control and Comparative Samples 3-6 to 3-8 gave undesirable grayish colors and low maximum density values.

EXAMPLE 4

The procedure of Example 1 was repeated, except that compounds of general formula (II) were used as the compounds to be incorporated in the processing composition.

The resulting print color, maximum density and relative sensitivity (D=0.6) are shown in Table 4. The minimum density was invariably 0.10.

TABLE 4

| Sample No. | Compound | Color | Maximum Density | Relative Sensitivity | Remarks |
| --- | --- | --- | --- | --- | --- |
| 4-1 | II-1 | Lacquer Black | 1.70 | 100 | Invention |
| 4-2 | II-2 | " | 1.72 | 98 | " |
| 4-3 | II-3 | " | 1.70 | 100 | " |
| 4-4 | II-9 | " | 1.68 | 102 | " |
| 4-5 | II-10 | " | 1.70 | 100 | " |
| 4-6 | II-15 | " | 1.65 | 104 | " |
| 4-7 | II-16 | " | 1.68 | 100 | " |
| 4-8 | II-20 | " | 1.65 | 104 | " |
| 4-9 | II-21 | " | 1.65 | 104 | " |
| 4-10 | No Addition | Bluish Gray | 1.60 | 100 | Control |
| 4-11 | 2,5-Mercapto-benzimidazole | Gray | 1.05 | 115 | Comparison |
| 4-12 | 2,5-Mercapto-benzothiazole | " | 0.98 | 120 | " |
| 4-13 | 2,5-Mercapto-benzoxazole | " | 1.02 | 115 | " |

As regards the metallic gloss of the print surface after separation at 5 minutes, only Control Sample 4-10 showed a slight metallic gloss. None of the other samples showed a metallic gloss.

It is apparent from Table 4 that with Samples 4-1 to 4-9 containing compounds of this invention a lacquer black color and high maximum density values were obtained. The maximum density values obtained with Samples 4-1 to 4-9 are higher than the Dmax of "no addition" Control 4-10.

EXAMPLE 5

In the silver iodobromide emulsion layer of the photosensitive sheet according to Example 1, there was incorporated 0.05 mg/m² of one of the compounds listed in Table 5. A processing composition was prepared in the same manner as in Example 1, except that a compound according to the present invention was not used. The processing composition was spread between the sheets in the same manner as in Example 1. The results are shown in Table 5.

TABLE 5

| Sample No. | Compound | Color | Maximum Density | Relative Sensitivity | Remarks |
| --- | --- | --- | --- | --- | --- |
| 5-1 | II-1 | Lacquer Black | 1.65 | 100 | Invention |
| 5-2 | II-2 | " | 1.63 | 102 | " |
| 5-3 | II-3 | " | 1.65 | 100 | " |
| 5-4 | II-10 | " | 1.65 | 100 | " |
| 5-5 | II-16 | " | 1.63 | 102 | " |
| 5-6 | No Addition | Bluish Gray | 1.60 | 100 | Control |
| 5-7 | 2-Mercapto-benzimidazole | Gray | 0.85 | 115 | Comparison |
| 5-8 | 2-Mercapto-benzothiazole | " | 0.80 | 118 | " |

It is apparent from Table 5 that with Samples 5-1 to 5-5 containing compounds according to this invention a lacquer black color and high maximum density values were obtained.

EXAMPLE 6

In the intermediate layer of the image receiving sheet described in Example 1, one of the compounds listed in Table 6 was incorporated at a level of 3 mg/m². A processing composition was prepared in the same manner as in Example 1, except that a compound of this invention was not used.

The above processing composition was spread between the sheets in the same manner as in Example 1. The results are shown in Table 6.

TABLE 6

| Sample No. | Compound | Color | Maximum Density | Relative Sensitivity | Remarks |
| --- | --- | --- | --- | --- | --- |
| 6-1 | II-1 | Lacquer Black | 1.65 | 100 | Invention |
| 6-2 | II-2 | " | 1.65 | 102 | " |
| 6-3 | II-3 | " | 1.64 | 100 | " |
| 6-4 | II-10 | " | 1.65 | 103 | " |
| 6-5 | II-16 | " | 1.63 | 105 | " |
| 6-6 | No Addition | Bluish Gray | 1.60 | 100 | Control |
| 6-7 | 2-Mercapto-benzimidazole | Gray | 0.85 | 135 | Comparison |
| 6-8 | 2-Mercapto-benzothiazole | " | 0.80 | 140 | " |

It is apparent from Table 6 that with Samples 6-1 to 6-5 containing compounds according to this invention a lacquer black color and high maximum density values were obtained. In contrast, Comparison Samples 3-7 and 3-8 gave an unsatisfactory gray color and low maximum density values.

EXAMPLE 7

The procedure of Example 1 was repeated, except that 0.2 g of compounds of general formula (III) were used as the compounds to be incorporated in the processing composition.

The resulting color, maximum density and relative sensitivity (D=0.6) are shown in Table 7. In all cases, the minimum density value was 0.10.

$mg/m^2$. A processing composition was prepared in the same manner as in Example 4, except that compounds of the present invention were not used. This processing composition was spread between the sheets in the same manner as in Example 1. The results are shown in Table 8.

TABLE 7

| Sample No. | Compound | Color | Maximum Density | Relative Sensitivity | Remarks |
|---|---|---|---|---|---|
| 7-1 | III-1 | Lacquer Black | 1.78 | 98 | Invention |
| 7-2 | III-2 | " | 1.75 | 103 | " |
| 7-3 | III-4 | " | 1.82 | 100 | " |
| 7-4 | III-5 | " | 1.83 | 100 | " |
| 7-5 | III-9 | " | 1.80 | 100 | " |
| 7-6 | III-12 | " | 1.83 | 100 | " |
| 7-7 | III-13 | " | 1.83 | 100 | " |
| 7-8 | III-14 | " | 1.68 | 93 | " |
| 7-9 | III-16 | " | 1.65 | 105 | " |
| 7-10 | III-17 | " | 1.78 | 102 | " |
| 7-11 | III-22 | " | 1.75 | 98 | " |
| 7-12 | III-25 | " | 1.75 | 98 | " |
| 7-13 | No Addition | Bluish Gray | 1.60 | 100 | Control |
| 7-14 | 1-Phenylmercapto-tetrazole | Gray | 0.48 | — | Comparison |
| 7-15 | 1-Phenylmercapto-triazole | " | 0.98 | 138 | " |
| 7-16 | 1-Phenylmercapto-imidazole | " | 1.15 | 115 | " |

In regard to the metallic gloss of the print surface after separation at 5 minutes, only the "no addition" control sample showed a slight metallic gloss. None of the other samples exhibited such a gloss.

It is apparent from Table 7 that with Samples 7-1 to 7-12 containing compounds according to this invention a lacquer black color and high maximum densities were obtained. The maximum density values obtained with the samples containing the compounds of the present invention are higher than the density value of "no addition" Control Sample 7-13.

EXAMPLE 8

In the silver iodobromide emulsion layer of the photosensitive sheet described in Example 1, one of the compounds listed in Table 8 was added at a level of 0.1

TABLE 8

| Sample No. | Compound | Color | Maximum Density | Relative Sensitivity | Remarks |
|---|---|---|---|---|---|
| 8-1 | III-1 | Lacquer Black | 1.73 | 100 | Invention |
| 8-2 | III-9 | " | 1.78 | 101 | " |
| 8-3 | III-12 | " | 1.80 | 101 | " |
| 8-4 | III-22 | " | 1.71 | 100 | " |
| 8-5 | III-4 | " | 1.70 | 98 | " |
| 8-6 | No Addition | Bluish Gray | 1.60 | 100 | Control |
| 8-7 | 1-Phenylmercapto-tetrazole | Gray | 0.25 | — | Comparison |
| 8-8 | 1-Phenylmercapto-triazole | " | 0.56 | — | " |
| 8-9 | 1-Phenylmercapto-imidazole | " | 0.78 | — | " |

It is apparent from Table 8 that with Samples 8-1 to 8-5 containing compounds according to this invention a lacquer black color and high maximum density values were obtained.

EXAMPLE 9

In the intermediate layer of the image receiving sheet described in Example 1, one of the compounds listed in Table 9 was incorporated at a level of 5 $mg/m^2$. A processing composition was prepared in the same manner as in Example 1, except that a compound of the present invention was not used.

The above processing composition was spread between the sheets in the same manner as in Example 1. The results are shown in Table 9.

TABLE 9

| Sample No. | Compound | Color | Maximum Density | Relative Sensitivity | Remarks |
|---|---|---|---|---|---|
| 9-1 | III-1 | Lacquer Black | 1.68 | 100 | Invention |
| 9-2 | III-9 | " | 1.72 | 101 | " |
| 9-3 | III-12 | " | 1.74 | 101 | " |
| 9-4 | III-22 | " | 1.67 | 100 | " |
| 9-5 | III-28 | " | 1.65 | 100 | " |
| 9-6 | No Addition | Bluish Gray | 1.60 | 100 | Control |
| 9-7 | 1-Phenylmercapto-tetrazole | Gray | 0.26 | — | Comparison |
| 9-8 | 1-Phenylmercapto-triazole | " | 0.72 | — | " |

TABLE 9-continued

| Sample No. | Compound | Color | Maximum Density | Relative Sensitivity | Remarks |
|---|---|---|---|---|---|
| 9-9 | 1-Phenylmercapto-imidazole | " | 0.93 | 132 | " |

It is apparent from Table 9 that with Samples 9-1 to 9-5 containing compounds according to this invention a lacquer black color and high maximum density values were obtained. In contrast, Comparison Samples 9-7 to 9-9 gave an unsatisfactory gray color and low maximum density values.

While the invention has been described in detail and with reference to specific embodiments thereof, it will be apparent to one skilled in the art that various changes and modifications can be made therein without departing from the spirit and scope thereof.

What is claimed is:

1. A method of forming a silver salt diffusion transfer image, comprising: developing an imagewise exposed photosensitive silver halide emulsion layer with a developing agent and a silver halide solvent in the presence of an alkali to thereby convert at least a portion of unexposed silver halide in said emulsion layer to a diffusible silver complex salt and transferring at least a portion of said silver complex salt into a silver precipitating agent-containing image receiving layer to form an image in said image receiving layer, wherein said image is formed in the presence of a compound selected from the group consisting of compounds of the following general formulae (I), (II) and (III):

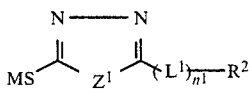 (I)

wherein $Z^1$ is a sulfur atom, an oxygen atom or

$R^3$ is a hydrogen atom, a substituted or unsubstituted alkyl group with the proviso that the substituent is not a sulfo or carboxyl group, or a substituted or unsubstituted aryl group with the proviso that the substituent is not a sulfo or carboxyl group;

$R^2$ is an organic group containing at least one sulfo or carboxyl group;

$L^1$ is —CONR—, —NRCO—, —SO$_2$NR—, —NRSO$_2$—, —OCO—, —COO—, —S—, —NR—, —CO—, —SO—, —SO$_2$—, —OCOO—, —NRCONR$^1$—, —NRCOO—, —OCONR—, or —NRSO$_2$NR$^1$—, wherein R and R$^1$, which may be the same or different, are selected from a hydrogen atom, an alkyl group or an aryl group;

$n^1$ is 0 or 1; and

M is a hydrogen atom, an alkali metal atom, a quaternary ammonium group or a quaternary phosphonium group;

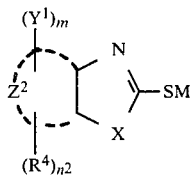 (II)

wherein X is

a selenium atom, a sulfur atom or an oxygen atom, wherein $R^7$ is a hydrogen atom or an alkyl group;

$R^4$ is a substituent group;

$Z^2$ is an atomic group necessary to form a carbocyclic or heterocyclic ring;

$Y^1$ is a carboxyl group or a sulfo group;

M is a hydrogen atom, an alkali metal atom, a quaternary ammonium group or a quaternary phosphonium group;

m is a whole number of 1 to 3; and $n^2$ is a whole number of 0 to 2; and

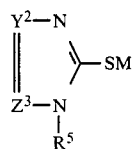 (III)

wherein $Y^2$ and $Z^3$, which may be the same or different, are N or CR$^6$ wherein R$^6$ is a hydrogen atom, a substituted or unsubstituted alkyl group, or a substituted or unsubstituted aryl group;

$R^5$ is an alkyl group substituted by at least one of SO$_3$M$^1$ or COOM$^1$ group or an aryl group substituted by at least one of SO$_3$M$^1$ or COOM$^1$ group;

M and M$^1$, which may be the same or different, are a hydrogen atom, an alkali metal atom, a quaternary ammonium group or a quaternary phosphonium group.

2. A method of forming a silver halide diffusion transfer image according to claim 1, wherein the image is formed in the presence of a compound of general formula (I).

3. A method of forming a silver halide diffusion transfer image according to claim 1, wherein the image is formed in the presence of a compound of general formula (II).

4. A method of forming a silver halide diffusion transfer image according to claim 1, wherein the image is formed in the presence of a compound of general formula (III).

5. A method of forming a silver halide diffusion transfer image according to claim 1, wherein R and R$^1$ are selected from a hydrogen atom, a lower alkyl group or a phenyl group;

$R^2$ is an alkyl group containing 1 to 20 carbon atoms or an aryl group containing 6 to 20 carbon atoms containing said at least one sulfo or carboxyl group which may be further substituted by alkyl groups, aryl groups, halogen atoms, alkoxy groups, carbamido groups, sulfonamido groups, hydroxy groups and sulfamoyl groups;

$L^1$ is —S—, —O—, —N=, —CO—, —SO— or —SO$_2$—; and $R^3$ is a hydrogen atom, a substituted or unsubstituted alkyl group containing 1 to 20 carbon atoms, or a substituted or unsubstituted aryl group containing 6 to 20 carbon atoms, wherein said substituents are selected from alkyl groups, aryl groups, halogen atoms, alkoxy groups, carbamido groups, sulfonamido groups, hydroxy groups and sulfamoyl groups.

6. A method of forming a silver halide diffusion transfer image according to claim 1, wherein $R^4$ is a halogen atom, a substituted or unsubstituted alkyl group, a substituted or unsubstituted aryl group, a substituted or unsubstituted alkoxy group, an aryloxy group, a sulfonyl group, a sulfonamido group, a sulfamoyl group, a carbamoyl group, an amido group, a ureido group, an aryloxy- or alkoxycarbonylamino group, an aryloxy- or alkoxycarbonyl group, a cyano group, a hydroxy group, a carboxyl group, a sulfo group or a nitro group;

$Z^2$ forms a 5-membered, 6-membered or 7-membered carbocyclic ring or a 5-membered, 6-membered or 7-membered heterocyclic ring containing one or more atoms selected from the group consisting of nitrogen, oxygen and sulfur atoms; and the sum of m and n is a whole number of 1 to 4.

7. A method of forming a silver halide diffusion transfer image according to claim 6, wherein $R^7$ is a hydrogen atom.

8. A method of forming a silver halide diffusion transfer image according to claim 1, wherein $R^5$ contains less than 20 carbon atoms and in addition to being substituted by at least one of an $SO_2M^1$ or $COOM^1$ group, may be further substituted by substituents selected from the group consisting of a halogen atom, alkoxy groups, aryloxy groups, amido groups, carbamoyl groups, sulfonamido groups, sulfamoyl groups, a cyano group, a hydroxy group, aryl groups and alkoxycarbonyl groups.

9. A method of forming a silver halide diffusion transfer image according to claim 8, wherein the group represented by $R^5$ contains 1 to 10 carbon atoms.

10. A method of forming a silver halide diffusion transfer image according to claim 1, wherein at least one compound represented by the formula (I), (II) or (III) is contained in a photosensitive element which contains said emulsion layer in an amount of $10^{-5}$ to 0.5 g per square meter of the face of the element, in an image receiving element which contains said image receiving layer in an amount of $10^{-4}$ to 0.5 g per square meter of the face of the element, or in a processing composition in an amount of $10^{-4}$ to 1 g per 100 g of processing composition.

* * * * *